United States Patent
Shur et al.

(10) Patent No.: US 10,688,312 B2
(45) Date of Patent: Jun. 23, 2020

(54) MEDICAL DEVICE WITH RADIATION DELIVERY

(71) Applicant: Sensor Electronic Technology, Inc., Columbia, SC (US)

(72) Inventors: Michael Shur, Latham, NY (US); Alexander Dobrinsky, Loudonville, NY (US)

(73) Assignee: Sensor Electronic Technology, Inc., Columbia, SC (US)

(*) Notice: Subject to any disclaimer, the term of this patent is extended or adjusted under 35 U.S.C. 154(b) by 453 days.

(21) Appl. No.: 15/388,296

(22) Filed: Dec. 22, 2016

(65) Prior Publication Data

US 2017/0189711 A1 Jul. 6, 2017

Related U.S. Application Data (60) Provisional application No. 62/273,545, filed on Dec. 31, 2015.

(51) Int. Cl.
*A61N 5/06* (2006.01)

(52) U.S. Cl.
CPC .......... *A61N 5/0601* (2013.01); *A61N 5/062* (2013.01); *A61N 5/0624* (2013.01); *A61N 2005/063* (2013.01); *A61N 2005/0612* (2013.01); *A61N 2005/0626* (2013.01); *A61N 2005/0651* (2013.01); *A61N 2005/0659* (2013.01); *A61N 2005/0661* (2013.01)

(58) Field of Classification Search
CPC .... A61N 5/0601; A61N 5/062; A61N 5/0624; A61N 2005/0626; A61N 2005/0659; A61N 2005/0661; A61N 2005/063; A61N 2005/0612; A61N 2005/0651
See application file for complete search history.

(56) References Cited

U.S. PATENT DOCUMENTS

| | | | |
|---|---|---|---|
| 7,553,456 B2 | 6/2009 | Gaska et al. | |
| 7,634,996 B2 | 12/2009 | Gaska et al. | |
| 8,277,734 B2 | 10/2012 | Koudymov et al. | |
| 8,980,178 B2 | 3/2015 | Gaska et al. | |
| 9,006,680 B2 | 4/2015 | Bettles et al. | |
| 9,061,082 B2 | 6/2015 | Gaska et al. | |
| 9,108,045 B2* | 8/2015 | Sakamoto | A61N 5/062 |
| 9,138,499 B2 | 9/2015 | Bettles et al. | |
| 9,179,703 B2 | 11/2015 | Shur et al. | |
| 9,572,903 B2 | 2/2017 | Dobrinsky et al. | |
| 9,603,960 B2 | 3/2017 | Dobrinsky et al. | |
| 9,687,577 B2 | 6/2017 | Dobrinsky et al. | |
| 9,718,706 B2 | 8/2017 | Smetona et al. | |
| 10,099,944 B2 | 10/2018 | Smetona et al. | |

(Continued)

OTHER PUBLICATIONS

"Valo Curing Light," Ultradent Products, Inc., downloaded from https://www.ultradent.com on Dec. 19, 2016, 10 pages.

*Primary Examiner* — Rex R Holmes
(74) *Attorney, Agent, or Firm* — LaBatt, LLC (57) ABSTRACT

Medical devices capable of delivering and/or sensing electromagnetic radiation within an organism body are described. Placement of a location for delivering and/or sending the electromagnetic radiation is done through the skin of the organism body. Devices described include a needle with a wave guiding structure configured to direct the electromagnetic radiation to/from a location within the organism body.

20 Claims, 6 Drawing Sheets

(56) References Cited

U.S. PATENT DOCUMENTS

| | | | |
|---|---|---|---|
| 2012/0041479 A1* | 2/2012 | Basore, Jr. | A61L 24/001 606/213 |
| 2013/0048545 A1 | 2/2013 | Shatalov et al. | |
| 2013/0261368 A1* | 10/2013 | Schwartz | A61N 5/1027 600/1 |
| 2014/0060094 A1 | 3/2014 | Shur et al. | |
| 2014/0060095 A1 | 3/2014 | Shur et al. | |
| 2014/0060096 A1 | 3/2014 | Shur et al. | |
| 2014/0060104 A1 | 3/2014 | Shur et al. | |
| 2014/0202962 A1 | 7/2014 | Bilenko et al. | |
| 2015/0008167 A1 | 1/2015 | Shturm et al. | |
| 2015/0069270 A1 | 3/2015 | Shur et al. | |
| 2015/0165079 A1 | 6/2015 | Shur et al. | |
| 2015/0196197 A1* | 7/2015 | Kienzle | A61B 1/042 600/478 |
| 2015/0217011 A1 | 8/2015 | Bettles et al. | |
| 2015/0265826 A1* | 9/2015 | Dudley | A61B 17/1327 604/403 |
| 2015/0273236 A1* | 10/2015 | Rogers | A61N 5/0624 607/80 |
| 2015/0297767 A1 | 10/2015 | Gaska et al. | |
| 2015/0336810 A1 | 11/2015 | Smetona et al. | |
| 2016/0000953 A1 | 1/2016 | Bettles et al. | |
| 2016/0058020 A1 | 3/2016 | Shur et al. | |
| 2016/0089530 A1* | 3/2016 | Sathe | A61M 39/20 604/533 |
| 2016/0114186 A1 | 4/2016 | Dobrinsky et al. | |
| 2016/0128526 A1 | 5/2016 | Dobrinsky et al. | |
| 2016/0324996 A1 | 11/2016 | Bilenko et al. | |
| 2017/0057842 A1 | 3/2017 | Dobrinsky et al. | |
| 2017/0100494 A1 | 4/2017 | Dobrinsky et al. | |
| 2017/0100495 A1 | 4/2017 | Shur et al. | |
| 2017/0100496 A1 | 4/2017 | Shur et al. | |

\* cited by examiner

MEDICAL DEVICE WITH RADIATION DELIVERY

REFERENCE TO RELATED APPLICATIONS

The current application claims the benefit of U.S. Provisional Application No. 62/273,545, which was filed on 31 Dec. 2015, and which is hereby incorporated by reference.

TECHNICAL FIELD

The disclosure relates generally to medical devices, and more particularly, to a medical device capable of delivering electromagnetic radiation within an organism body as part of a medical procedure.

BACKGROUND ART

Ultraviolet radiation has been proposed for use in cleaning medical equipment while it is being utilized. For example, systems for cleaning a medical tube with ultraviolet radiation while it remains in place have been proposed. Such tubes, when located internally during use, are typically inserted through an orifice of the body. The primary purpose of such tubes is the delivery or extraction of fluids to or from the body.

Electromagnetic radiation also has been used in dentistry, e.g., to provide for curing of a glue used in a dental appliance. In this case, a medical professional uses a hand-held instrument to move a radiation source to illuminate a desired location in a patient's mouth.

SUMMARY OF THE INVENTION

Aspects of the invention provide a medical device capable of delivering and/or sensing electromagnetic radiation within an organism body. Placement of a location for delivering and/or sending the electromagnetic radiation is done through the skin of the organism body. An illustrative device described herein includes a needle with a wave guiding structure configured to direct the electromagnetic radiation to/from a location within the organism body.

A first aspect of the invention provides a device comprising: a hypodermic needle configured to be inserted subcutaneously into an organism body; a set of radiation sources configured to generate electromagnetic radiation; and means for directing the electromagnetic radiation generated by the set of radiation sources to a location adjacent to a hollow end of the hypodermic needle.

A second aspect of the invention provides a system comprising: a set of radiation sources configured to generate electromagnetic radiation; means for placing an emission location for the electromagnetic radiation to a target location within an organism body through the skin of the organism body; and a computer system configured to operate the set of radiation sources to perform a medical procedure on the organism body using the electromagnetic radiation.

A third aspect of the invention provides a device comprising: a syringe configured to store a fluid; a set of radiation sources configured to generate electromagnetic radiation; a needle fluidly connected with the syringe, wherein the syringe is configured to at least one of: deliver or acquire, fluid through a hollow end in the needle, and wherein the needle includes a wave guiding structure to deliver electromagnetic radiation to a location adjacent to the hollow end in the needle.

Other aspects of the invention provide methods, systems, program products, and methods of using and generating each, which include and/or implement some or all of the actions described herein. The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a medical device capable of delivering and/or sensing electromagnetic radiation within an organism body. Placement of a location for delivering and/or sending the electromagnetic radiation is done through the skin of the organism body. An illustrative device described herein includes a needle with a wave guiding structure configured to direct the electromagnetic radiation to/from a location within the organism body.

As used herein, unless otherwise noted, the term "set" means one or more (i.e., at least one) and the phrase "any solution" means any now known or later developed solution. It is understood that, unless otherwise specified, each value is approximate and each range of values included herein is inclusive of the end values defining the range. As used herein, unless otherwise noted, the term "approximately" is inclusive of values within +/− ten percent of the stated value, while the term "substantially" is inclusive of values within +/− five percent of the stated value. Unless otherwise stated, two values are "similar" when the smaller value is within +/− twenty-five percent of the larger value.

As also used herein, a material is transparent when the material allows at least ten percent of radiation having a target wavelength, which is radiated at a normal incidence to an interface of the material, to pass there through. Furthermore, as used herein, a material is reflective when the material reflects at least ten percent of radiation having a target wavelength, which is radiated at a normal incidence to an interface of the material. In an embodiment, the target wavelength of the radiation corresponds to a wavelength of radiation emitted or sensed (e.g., peak wavelength +/− five nanometers) by an active region of an optoelectronic device during operation of the device. The wavelength can be measured in a material of consideration and can depend on a refractive index of the material.

Figure 1:
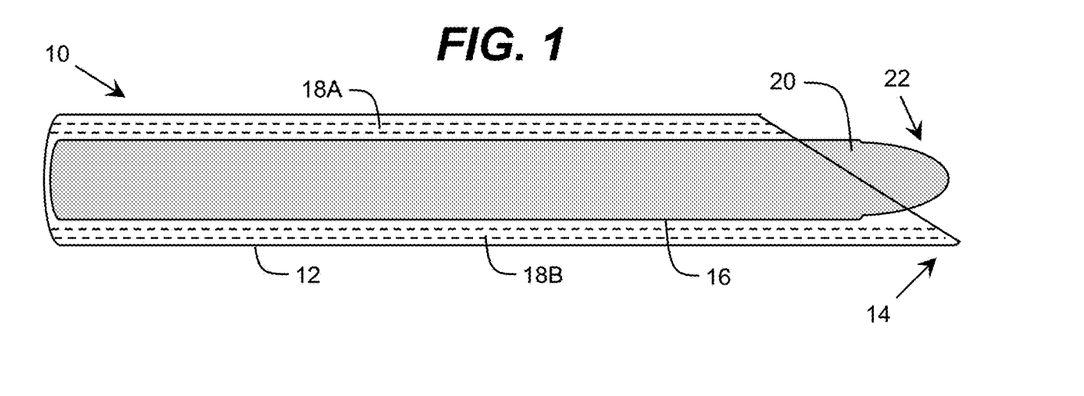
FIG. 1 shows an illustrative needle according to an embodiment.

Turning to the drawings, FIG. 1 shows an illustrative needle 10 (e.g., a hypodermic needle) according to an embodiment. In an embodiment, the needle 10 comprises a hollow tube 12 including an insertion end 14, which can be beveled to facilitate subcutaneous (e.g., through the skin) insertion of the insertion end 14 into an organism body. The hollow tube 12 can be formed of any material suitable for use in an application described herein. In an illustrative embodiment, the hollow tube 12 can be formed of stainless-steel, titanium, or other biologically compatible metal alloys. The hollow tube 12 can be of any gauge and any length suitable for an application described herein. Similarly, the insertion end 14 can have any of various bevel inclinations suitable for use when inserting the insertion end 14 of the needle 10 into the skin of an organism body. Regardless, it is understood that inclusion of a beveled insertion end 14 may not be necessary in all embodiments.

The hollow tube 12 is shown including a wave guiding structure 20 located therein. The wave guiding structure 20 can comprise any type of structure 20 which is suitable for directing electromagnetic radiation to a location adjacent to the insertion end 14 of the needle 10. In an embodiment, the wave guiding structure 20 comprises optical fiber, which is located within the hollow tube 12 of the needle 10. As illustrated, the optical fiber can include a tapered end 22, which can partially protrude from the insertion end 14 of the needle 10. Alternatively, the optical fiber can terminate within the hollow tube 12 or terminate having an angle aligned with the insertion end 14 of the needle 10 (e.g., along the bevel angle).

An interior surface 18 of the hollow tube 12 can be configured to facilitate wave guiding the electromagnetic radiation through the hollow tube 12. For example, at least the interior surface 18 of the hollow tube 12 can be formed of a material reflective of the electromagnetic radiation, such as stainless-steel, polished aluminum, a fluoropolymer (e.g., fluorinated ethylene-propylene (EFEP), polytetrafluoroethylene (PTFE), ethylene-tetrafluoroethylene (ETFE), or the like), etc. In an embodiment, the wave guiding structure 20 comprises a fluid, such as air. In this case, the hollow tube 12 can remain hollow and the electromagnetic radiation can propagate through the hollow tube 12 before exiting the insertion end 14.

In an embodiment, the needle 10 can be configured to also deliver or extract a fluid to or from the organism body. Any bodily fluid can be extracted using the needle 10, including blood, urine, etc. Illustrative fluids that can be delivered to the organism body include a saline solution, a medicine containing fluid, a fluid containing magnetic or fluorescent nanoparticles or both, and/or the like. When the wave guiding structure 20 includes air, the hollow tube 12 can also be utilized during the delivery or extraction of the fluid. Alternatively, the walls of the hollow tube 12 can include one or more channels 18A, 18B, which provide for the flow of fluid therein. Such channels 18A, 18B can be included when the wave guiding structure 20 comprises an optical fiber or the like. In either case, the needle 10 can be utilized to emit electromagnetic radiation within the organism body before, during, and/or after the delivery or extraction of the fluid. Additionally, while the wave guiding structure 20 is shown located in the large opening of the hollow tube 12, it is understood that embodiments can include wave guiding structure(s) located in the channels 18A, 18B embedded within the walls of the hollow tube 12, while the large opening can be used for the extraction or delivery of the fluid.

Figure 2A:
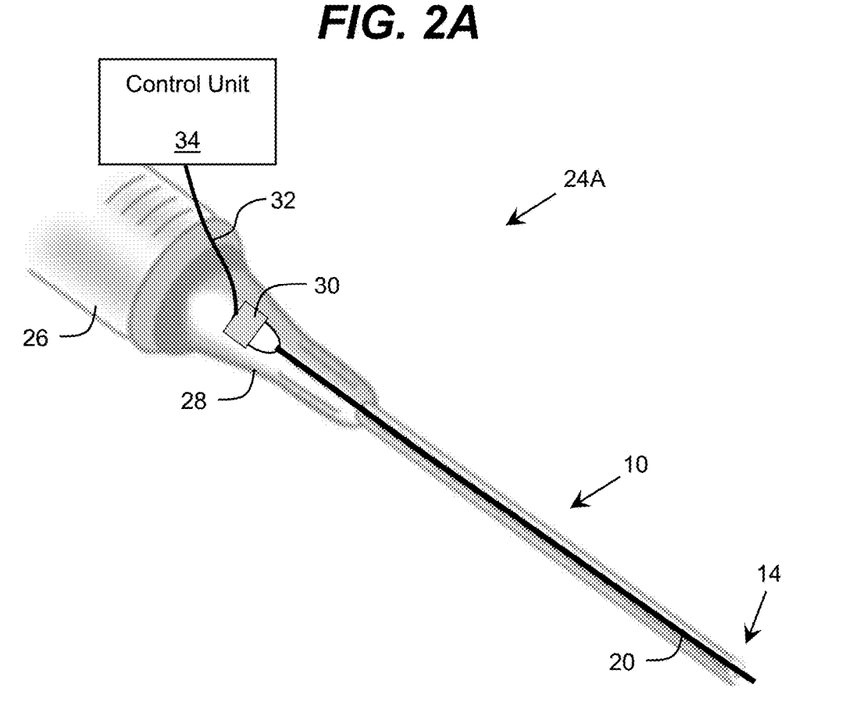
FIGS. 2A and 2B show illustrative devices including a needle according to embodiments.
Figures 2B, 3A, 3B:
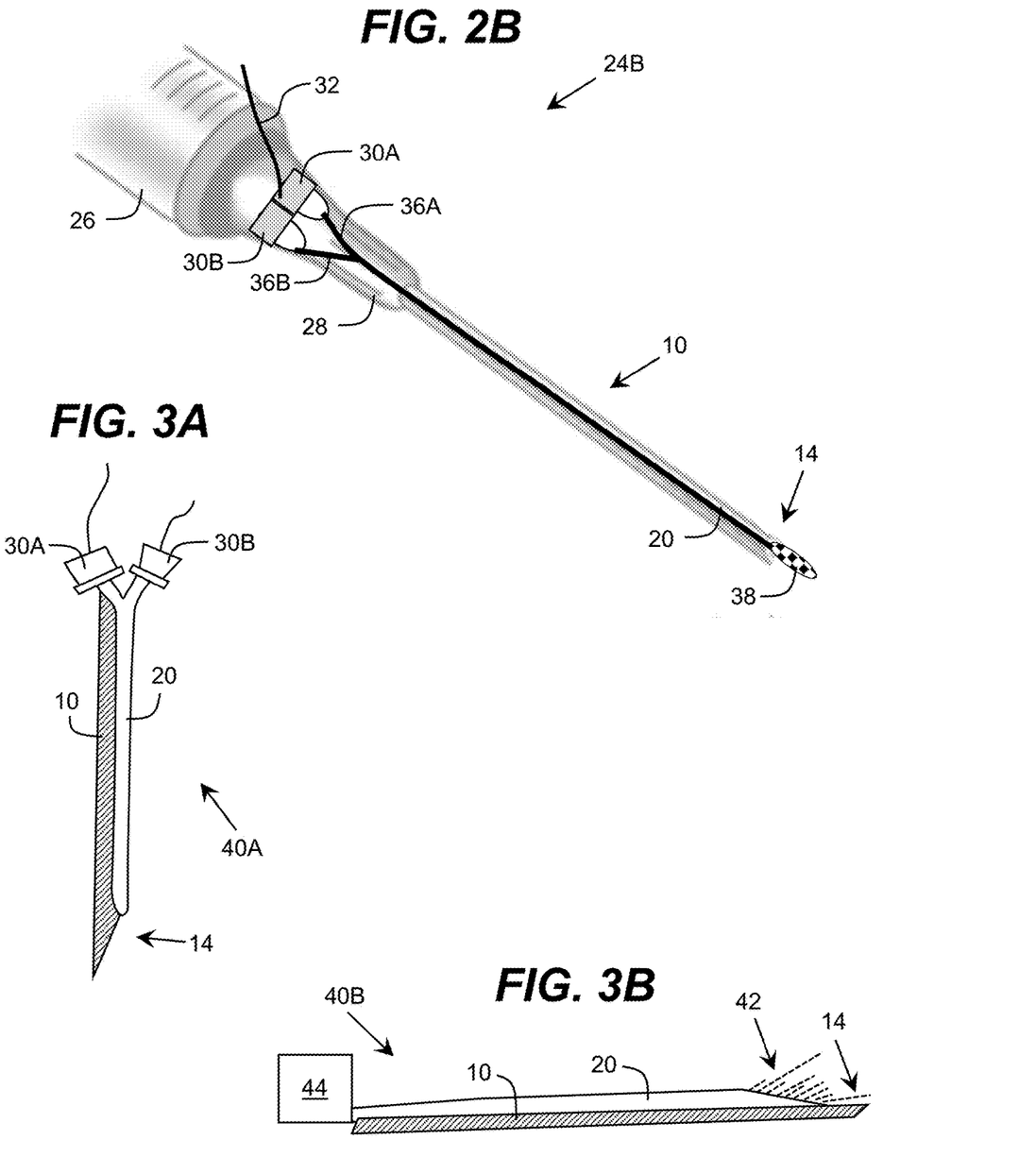
FIGS. 3A and 3B show additional illustrative devices according to embodiments.

FIGS. 2A and 2B show illustrative devices 24A, 24B including a needle 10 according to embodiments. In each case, the needle 10 can be configured similar to the needle 10 shown in FIG. 1. Each device 24A, 24B includes a syringe 26 fluidly attached to the needle 10 by a connector 28. The syringe 26 and connector 28 can be configured and operate as known in the art. To this extent, the syringe 26 can include a tube defining an enclosed volume for storing a fluid, and a mechanism (e.g., a plunger) for drawing the fluid into the enclosed volume and/or expelling fluid from the enclosed volume. An opening in the syringe 26 can be enclosed by the connector 28 (e.g., a Luer connector), which provides a fluid tight connection such that fluid must travel through the needle 10 when being drawn into or expelled from the enclosed volume of the syringe 26.

As illustrated in FIG. 2A, the needle 10 includes a wave guiding structure 20 located therein. Furthermore, the device 24A is shown including an optoelectronic device 30, which can be configured to generate electromagnetic radiation that is guided by the wave guiding structure 20 through the needle 10 before exiting the insertion end 14 of the needle 10. As illustrated, the optoelectronic device 30 can be located within the connector 28. For example, the optoelectronic device 30 can be mounted to and/or embedded in a material forming the connector 28. When the needle 10 is also used to in conjunction with delivering or extracting a fluid, the optoelectronic device 30 can be located so as not to impede the fluid flowing through a set of openings in the needle 10 and the opening in the syringe 26. Regardless, the connector 28 and the mounting configuration for the optoelectronic device 30 also can be configured to prevent the electromagnetic radiation from escaping through the connector 28 and/or from being directed up into the syringe 26. In an embodiment, the connector 28 can be formed of a metal or plastic, with at least a portion of an internal surface of the connector 28 being reflective of the electromagnetic radiation (e.g., coated with a reflective material).

It is understood that an optoelectronic device 30 can be configured to emit or sense electromagnetic radiation. In an embodiment, the optoelectronic device 30 is configured to operate as an emitting device, such as a light emitting diode (LED) or a laser diode (LD). Alternatively, the optoelectronic device 30 can be configured to operate as a light sensing device, such as a photodiode. Regardless, the electromagnetic radiation emitted (or sensed) by the optoelectronic device 30 can have a peak wavelength within any range of wavelengths, including visible light, ultraviolet radiation, deep ultraviolet radiation, infrared light, and/or the like. In an embodiment, the optoelectronic device 30 is configured to emit (or sense) radiation having a dominant wavelength within the ultraviolet range of wavelengths. Embodiments of optoelectronic devices 30 configured to emit electromagnetic radiation can emit radiation that is monochromatic (e.g., includes a single peak wavelength) or includes several different peak wavelengths. The wave guiding structure 20 can be configured based on the corresponding electromagnetic radiation to be transmitted there through. Illustrative wave guiding structures 20 can be formed of quartz, a fluoropolymer, silicon dioxide, and/or the like.

The device 24A can further include a control unit 34, which can operate the optoelectronic device 30. The control unit 34 can be operatively connected to the optoelectronic device 30 via an electrical wire 32, or the like, which provides power to the optoelectronic device 30. In an embodiment, the control unit 34 includes a power supply (e.g., a battery, connection to a power grid, and/or the like) as well as a mechanism for selectively turning the optoelectronic device 30 on or off (e.g., a switch). The control unit 34 can enable manual operation of the optoelectronic device 30 and/or automated operation of the optoelectronic device 30. In the latter case, the control unit 34 can include a computing device. The computing device can be fabricated from hardware or include a combination of hardware (e.g., a processor, memory, and one or more input/output devices, such as a transceiver) and software which programs the computing device to operate the optoelectronic device 30 according to a corresponding medical procedure. It is understood that alternative configurations are possible. For example, in an embodiment, the optoelectronic device 30 can include its own power supply and a wireless communications component, which enables the optoelectronic device 30 to be turned on and off by a control unit 34 in wireless communication therewith. An illustrative wireless communications solution is the Bluetooth wireless standard, which enables short range wireless communications between devices.

While shown separate from the syringe 26 and connector 28, it is understood that embodiments of the control unit 34 can be incorporated into one or both of the syringe 26 and connector 28. In an embodiment, the connector 28 can include a coupling mechanism (e.g., a male or female connector), which allows for a removable connection between the control unit 34 and the optoelectronic device 30. In this manner, the same control unit 34 can be utilized to control optoelectronic devices 30 in different connectors 28 and/or needles 10. Furthermore, an embodiment of the connector 28 can include an optical coupling mechanism for the wave guiding structure 20. In this case, the optoelectronic device 30 also can be implemented external of the connector 28 and be configured to generate radiation which is transmitted into a first wave guiding structure, which is subsequently optically coupled to the wave guiding structure 20 using any solution. Such configurations can be particularly useful when the control unit 34 includes a computing device and/or the connector 28 and needle 10 are configured for a single use.

In FIG. 2B, the device 24B is shown including multiple optoelectronic devices 30A, 30B located within the coupler 28. As illustrated, radiation output from both optoelectronic devices 30A, 30B can be wave guided by a corresponding wave guiding structure 36A, 36B, respectively, and merged via an optical coupling into the wave guiding structure 20 included in the needle 10. The optoelectronic devices 30A, 30B can be operatively coupled to the control unit 34 (FIG. 2A) using any solution, e.g., via an electrical conductor 32. The operative coupling can enable individual operation of the optoelectronic devices 30A, 30B and/or operation of the optoelectronic devices 30A, 30B as a group. In either case, the optoelectronic devices 30A, 30B can generate electromagnetic radiation having substantially the same or distinct peak wavelengths.

The device 24B also is shown including an optical element 38 located at the insertion end 14 of the needle 10. The optical element 38 can be optically coupled to the wave guiding structure 20 and can be configured to provide any desired optical function for radiation traveling through the wave guiding structure 20. For example, the optical element 38 can be a diffusive element, a lens, an optical modulator, and/or the like, which can manage distribution of the radiation being emitted from the wave guiding structure 20.

As described herein, embodiments of the needle 10 can enable the sensing and/or delivery of electromagnetic radiation from and/or to a location in an organism body. To this extent, the control unit 34 can receive data corresponding to sensed electromagnetic radiation (e.g., reflected or fluoresced) and adjust one or more aspects of the operation of the optoelectronic device(s) 30. For example, the control unit 34 can adjust a radiation intensity, a delivered dose, a target location, and/or the like, based on the information received regarding the location within the organism body. It is understood that while electromagnetic radiation-based feedback data is discussed, embodiments of a device described herein can include one or more alternative sensing devices for acquiring other data regarding the internal location of the organism body, which the control unit 34 can utilize to adjust operation of the optoelectronic device(s) 30.

Furthermore, various configurations of the needle 10 and wave guiding structure 20 are possible. FIGS. 3A and 3B show additional illustrative devices 40A, 40B, respectively, according to embodiments. In FIG. 3A, the device 40A is shown including two optoelectronic devices 30A, 30B optically coupled to a wave guiding structure 20. In this embodiment, one optoelectronic device can be configured to emit radiation, while the other optoelectronic device can be configured to sense radiation. For example, the optoelectronic device 30A can be an ultraviolet light emitting diode while the optoelectronic device 30B can be a fluorescence meter.

In the devices 40A, 40B, the wave guiding structure 20 is shown coupled to the needle 10, instead of being embedded therein. The wave guiding structure 20 can be coupled to the needle 10 using any solution, such as, a biologically compatible adhesive, soldering, and/or the like. The needle 10 can include a beveled insertion end 14 to facilitate inserting the needle 10 into an organism body. Embodiments of the needle 10 can be hollow, to enable the delivery and/or extraction of fluid, or be solid, in which case the needle is only utilized to locate the wave guiding structure 20 within the organism body. In FIG. 3B, the device 40B is shown including a wave guiding structure having a scattering region 42 for the electromagnetic radiation emitted therefrom. Embodiments of the wave guiding structure 20 can enable emission and/or acquisition of electromagnetic radiation only from an end region of the wave guiding structure 20 located adjacent to the insertion end 14 or in one or more locations along a length of the wave guiding structure 20 and needle 10.

Each optoelectronic device 30A, 30B of the device 40A can be permanently or removably attached to the wave guiding structure 20 using any solution. In the device 40B, a component 44 including any combination of optoelectronic devices (including one or more emitters and/or one or more detectors) can be permanently or removably attached to the wave guiding structure 20. In this case, the component 44 can include any wave guiding structures required for optically coupling the optoelectronic devices included therein, and the needle wave guiding structure 20 coupled to the needle 10 does not require any such optical coupling mechanisms.

Figure 4:
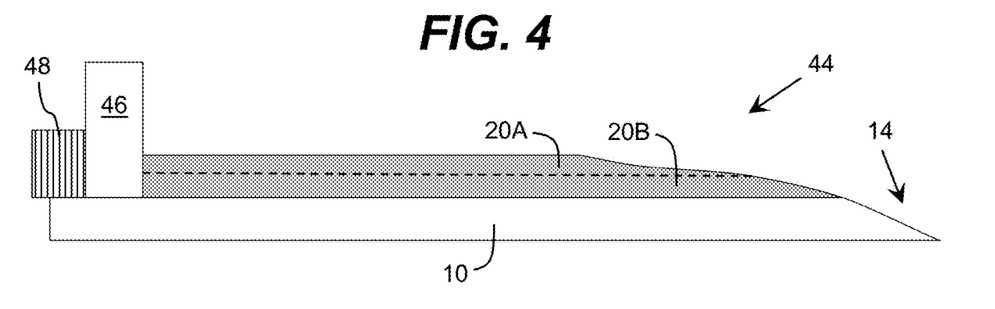
FIG. 4 shows still another illustrative device according to an embodiment.
Figure 5:
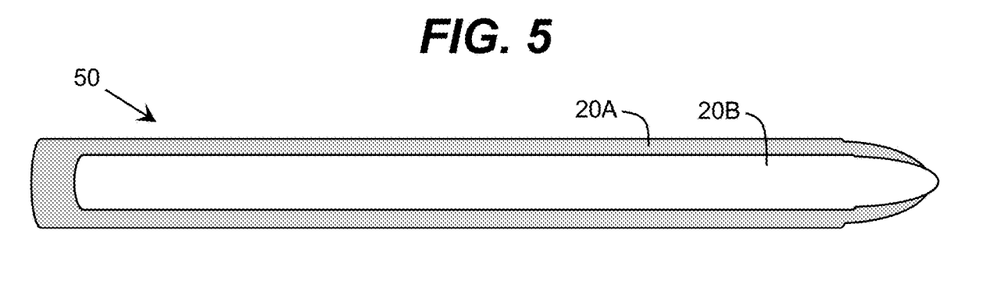
FIG. 5 shows an illustrative compound wave guiding structure according to an embodiment.

FIG. 4 shows still another illustrative device 44 according to an embodiment. The device 44 is shown including multiple wave guiding structures 20A, 20B coupled to a needle 10. As illustrated, the wave guiding structures 20A, 20B have beveled ends that are aligned with the beveled insertion end 14 of the needle 10. However, it is understood that this is only an illustrative configuration for including multiple wave guiding structures 20A, 20B. For example, FIG. 5 shows an illustrative compound wave guiding structure 50 including multiple, physically separate wave guiding structures 20A, 20B according to an embodiment. In an embodiment, the compound wave guiding structure 50 can be located in a hollow needle 10. For example, the compound wave guiding structure 50 can replace the wave guiding structure 20 shown in FIG. 1.

Regardless, using the device 44 shown in FIG. 4 as an example, each wave guiding structure 20A, 20B can be configured to provide wave guiding for a different purpose. For example, a first wave guiding structure 20A can provide wave guiding for radiation being emitted from a first optoelectronic device included within an optoelectronic component 46, while the second wave guiding structure 20B can be configured to provide wave guiding for radiation being sensed by a second optoelectronic device included within the optoelectronic component 46. However, it is understood that this is only illustrative, and both wave guiding components 20A, 20B can provide wave guiding for radiation being sensed or emitted by device(s) in the optoelectronic component 46. In an embodiment, each wave guiding component 20A, 20B can be configured differently, based on the corresponding type of electromagnetic radiation with which the wave guiding component 20A, 20B is configured to operate.

The optoelectronic component 46 can include one or more optoelectronic devices, each of which can be optically coupled to a corresponding wave guiding component 20A, 20B. Furthermore, the optoelectronic component 46 can include a power source for operating the optoelectronic device(s) as well as an interface for turning the optoelectronic device(s) on or off (e.g., a switch). Alternatively, one or more optoelectronic devices can be temporarily connected to the optoelectronic component 46 using a connector 48. In this case, the optoelectronic component 46 can include a set of standard optoelectronic devices, which can be extended via the connector 48 or include no optoelectronic devices, but only the power source and/or interface for operating the optoelectronic device(s) coupled to the connector 48.

Figure 6:
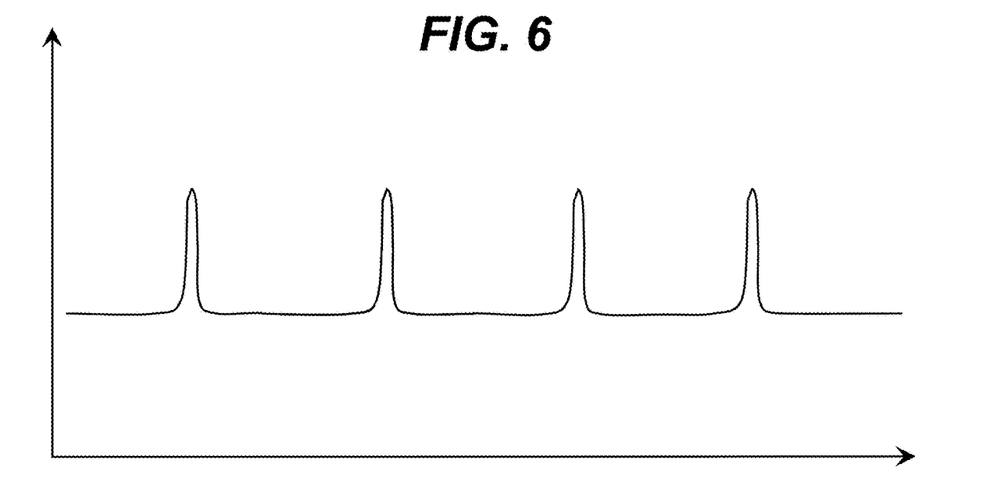
FIG. 6 shows an illustrative time sequence of operation of an optoelectronic device to emit radiation according to an embodiment.

The connector 48 also can provide an operable connection to a control unit 34 (FIG. 2A), which can include a computing device. The control unit 34 can include an interface that enables a user to select a procedure, which has an associated set of parameters for operating the optoelectronic device(s) of the device 44. When operated under control of a computing device, the optoelectronic device(s) described herein can be operated in a more complex, repeatable manner. For example, FIG. 6 shows an illustrative time sequence of operation of an optoelectronic device to emit radiation according to an embodiment. As illustrated, the optoelectronic device can be operated using a series of pulses followed by extended periods in which the device is off. In this manner, each pulse can deliver extra bright radiation. Pulsed operation can ensure a low power consumption by the optoelectronic device(s), can increase the sensitivity, provide an ability for acquiring additional information during the monitoring (e.g., via recording the time waveform of a response to each pulse), and/or the like. The pulses can be as short as a fraction of a picosecond with duty cycle ranges from milliseconds to minutes.

Embodiments of a device described herein can be utilized in conjunction with various medical procedures. As used herein, a medical procedure includes any procedure intended to provide medical treatment to an organism body and any procedure intended to provide medical evaluation or diagnosis of the organism body. Medical procedures include those procedures performed during the life of the organism and procedures performed post mortem.

For example, a device can include one or more optoelectronic devices configured to emit ultraviolet radiation (e.g., UVA, UVB, and/or UVC). In this case, the ultraviolet radiation can be used in medical procedures for photocatalyst reaction, disinfection, improving the production of vitamin D (e.g., when delivered to an area of the skin), and/or the like. The ultraviolet radiation can have a wavelength in a range between 200 nanometers and 400 nanometers in an illustrative embodiment. In another embodiment, a device can include one or more optoelectronic devices configured to emit infrared radiation including, for example, infrared laser radiation. In this case, the infrared radiation can be utilized for heating up and/or destroying cells within the organism body. Such an application can be used in conjunction with, for example, chemotherapy. In still another embodiment, the electromagnetic radiation can include one or more wavelengths of radiation used to activate a drug. For example, the drug can comprise several chemical elements activated by light (e.g., chemically reacted).

Figure 7:
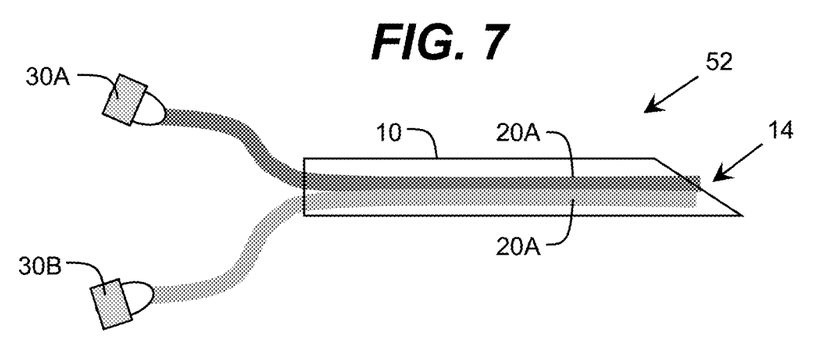
FIG. 7 shows a schematic of an illustrative device according to an embodiment.

In an illustrative embodiment, the device can be configured to be utilized at different times during a medical procedure. For example, FIG. 7 shows a schematic of an illustrative device 52 according to an embodiment. In this case, the device 52 includes two optoelectronic devices 30A, 30B, each of which can be optically coupled to a unique wave guiding structure 20A, 20B located in and/or attached to a needle 10. Alternatively, the wave guiding structures 20A, 20B can correspond to a single wave guiding structure that is alternately used by the optoelectronic devices 30A, 30B. Regardless, in a more particular illustrative embodiment, the optoelectronic device 30A can be operated to generate a high intensity electromagnetic radiation, which is configured to destroy tissue located adjacent to the insertion end 14 of the needle 10. Subsequently, the optoelectronic device 30b can be operated to generate electromagnetic radiation configured to activate a chemical (e.g., medicine) located near the insertion end 14 of the needle 10. The chemical can be delivered using any mechanism, including by the needle 10 and a syringe attached thereto.

Figure 8A:
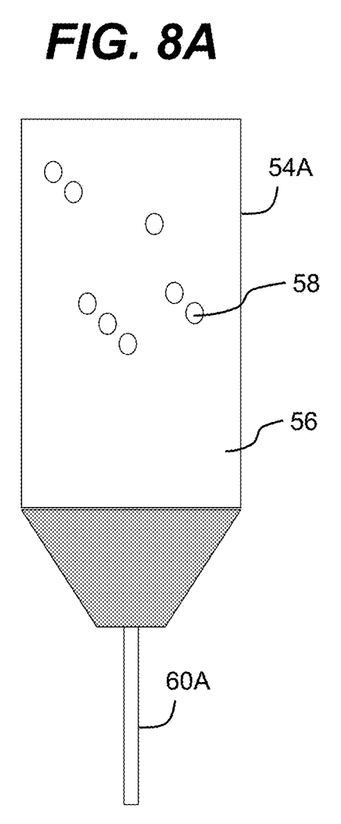
FIGS. 8A and 8B show illustrative containers with fluids, which can be utilized in conjunction with a device described herein, according to embodiments.
Figure 8B:
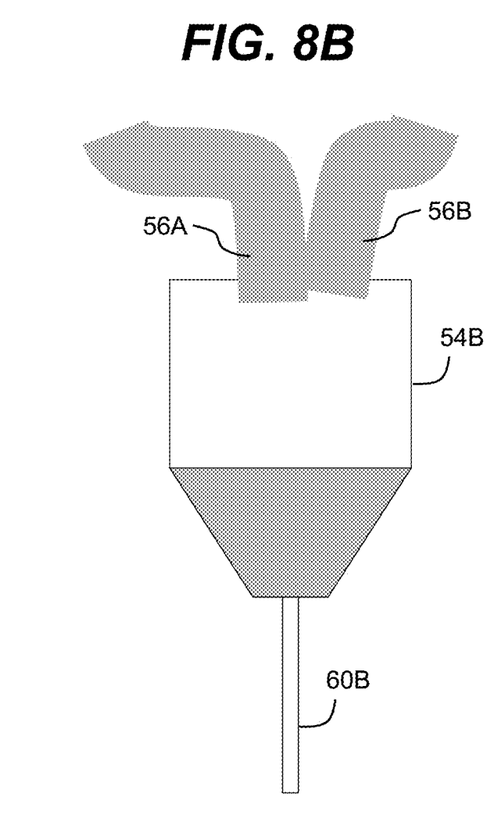

Embodiments of a device described herein can be utilized in conjunction with the delivery of various types of chemicals and fluids. To this extent, FIGS. 8A and 8B show illustrative containers 54A, 54B with fluids, which can be utilized in conjunction with a device described herein according to embodiments. In FIG. 8A, the container 54A is shown including a fluid 56, which includes nanoparticles 58 suspended therein. The fluid 56 can be utilized to deliver the nanoparticles 58 to a desired location within an organism body. The nanoparticles 58 can comprise, for example, gold or silver. In embodiments, one or both of the fluid 56 and the nanoparticles 58 (e.g., nanoshells) can include a medication. The fluid 56 and nanoparticles 58 can exit the container 54A along a tube 60A, which is fluidly connected to a needle described herein. To this extent, the needle can include one or more optoelectronic devices, which can, for example, be utilized to activate the medication included in the fluid 56 and/or nanoparticles 58. In FIG. 8B, two fluids 56A, 56B are mixed in the container 54B. The combined fluids 56A, 56B can exit the container 54B along the tube 60B, which is fluidly connected to a needle described herein. To this extent, the needle can include one or more optoelectronic devices, which can, for example, be utilized to activate a medication included in the combined fluids 56A, 56B. It is understood that these configurations are only illustrative, and other embodiments can include one or more optoelectronic devices used to emit electromagnetic radiation on the fluids while the fluids are within the containers 54A, 54B and/or the tubes 60A, 60B.

Figure 9A:
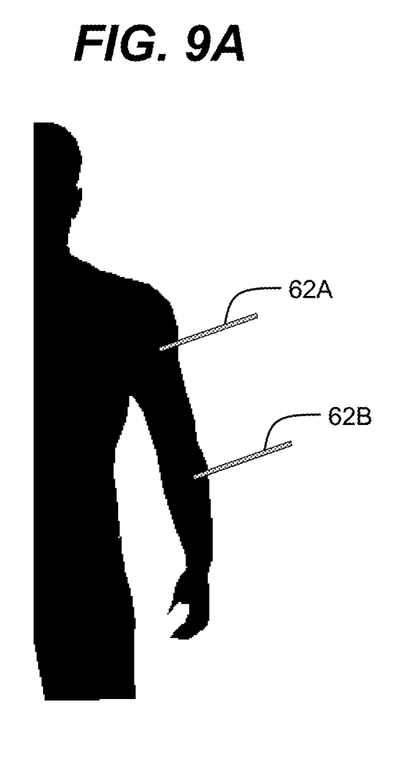
FIGS. 9A and 9B illustrate the use of multiple devices as part of medical procedures according to embodiments.
Figure 9B:
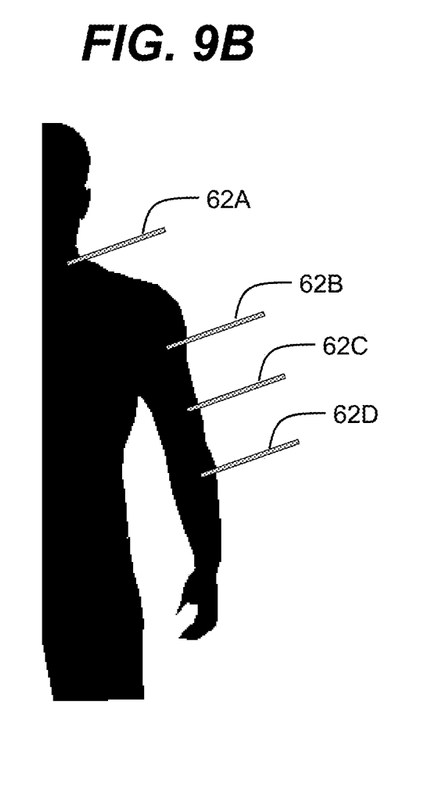

Furthermore, a medical procedure may utilize multiple devices described herein. For example, FIGS. 9A and 9B illustrate the use of multiple devices as part of medical procedures according to embodiments. In FIG. 9A, a first device 62A is utilized at a first location on an organism body, while a second device 62B is utilized at a second location on the organism body. In this case, the first device 62A can be utilized to introduce a treatment (e.g., electromagnetic radiation, a medicine, and/or the like), and the second device 62B can be used to evaluate an effect of the treatment (e.g., by sensing fluorescence) and/or activate the treatment (e.g., by introducing electromagnetic radiation).

In a more particular illustrative embodiment, the first device 62A can comprise an electromagnetic source, which induces fluorescence in a type of object being monitored, and the second device 62B can comprise a fluorescent sensor for acquiring data regarding the fluorescence induced by the first device 62A. In an illustrative medical procedure, a control unit 34 (FIG. 2A) can process fluorescence data acquired by the second device 62B and compare one or more attributes of the fluorescence data (e.g., spectra and/or intensity) with a pre-recorded etalon. The control unit 34 can adjust one or more parameters of the electromagnetic radiation delivered using the first device 62A to achieve desired fluorescence characteristics within a predetermined tolerance.

In another more particular illustrative embodiment, the first device 62A can comprise a medicine source, and the second device 62B can comprise a fluorescent sensor and/or electromagnetic source, which can be used to activate the medicine and/or acquire data regarding fluorescence induced by the medicine.

In FIG. 9B, four devices 62A-62D are shown, which can be used to perform a more complicated medical treatment. For example, the medical treatment can include one or more locations at which: a medicine is introduced; electromagnetic radiation is introduced; and/or electromagnetic radiation is sensed. In an illustrative embodiment of a medical treatment, the device 62A can be utilized to introduce a medicine, and the device 62B can be used to sense electromagnetic radiation, such as fluorescence. The device 62C can comprise an electromagnetic source, and the device 62D can comprise a second electromagnetic radiation sensor. It is understood that this configuration is only illustrative. For example numerous additional devices 62A-62D, e.g., up to 100 emitters and/or sensors, can be utilized in a medical treatment. In an embodiment, a system can include at least one source location for electromagnetic radiation, which is operated in a pulsed manner, and at least one fluorescence location at which fluorescence caused by the pulsed radiation is measured and a time between the pulse and corresponding detected fluorescence is measured and utilized in the medical procedure.

While various embodiments described herein have illustrated use of a needle to deliver and/or sense electromagnetic radiation to and/or from a desired location within an organism body, it is understood that the needle is only illustrative of various devices capable of placing an emission and/or sensing location for electromagnetic radiation at a target location within an organism body through the skin of the organism body.

Figure 10A:
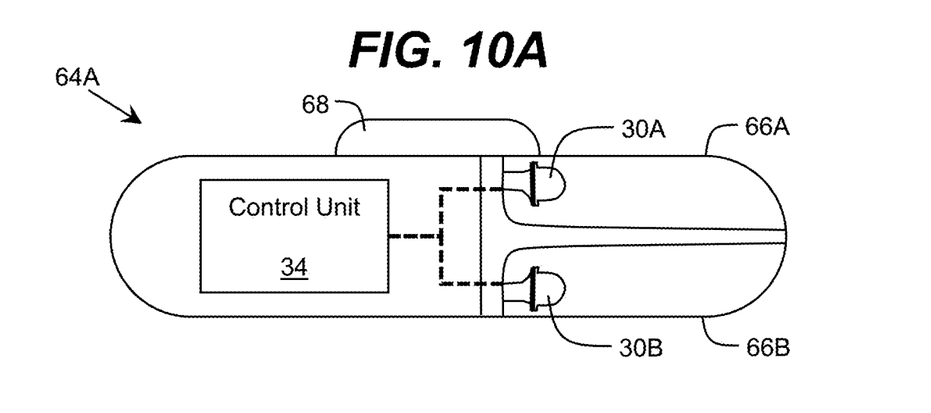
FIGS. 10A and 10B show illustrative optoelectronic medical devices according to embodiments.
Figure 10B:
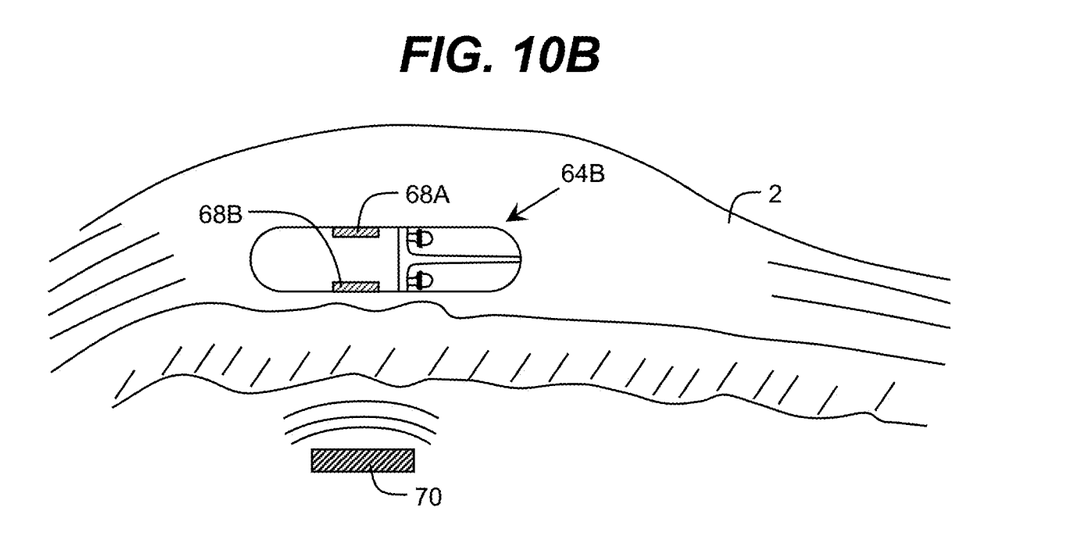

To this extent, FIGS. 10A and 10B show illustrative optoelectronic medical devices 64A, 64B according to embodiments. In FIG. 10A, the device 64A is shown including a control unit 34, which can be configured as described herein. In particular, the control unit 34 can include a computing device (e.g., a processor, memory, and one or more input/output devices), a wireless transceiver, a power source (e.g., a battery), and/or the like. The control unit 34 can be operatively connected to one or more optoelectronic devices 30A, 30B, which can be configured as described herein. Each optoelectronic device 30A, 30B can be protected from the ambient environment by being located within a transparent enclosure 66A, 66B, respectively.

In an illustrative embodiment, the optoelectronic devices 30A, 30B include an ultraviolet light source and a fluorescence measurement device. The control unit 34 can operate the optoelectronic devices 30A, 30B to evaluate one or more attributes of the ambient environment in which the optoelectronic medical device 64A is placed. Additionally, the optoelectronic medical device 64A is shown including a medicine delivery source 68. The medicine delivery source 68 can be configured to deliver a medication to a location of the optoelectronic medical device 64A using any solution. For example, the medication can be released at once, slowly over time, and/or the like. Release of the medication can be done automatically (e.g., as a result of a capsule disintegrating, or under the control of the control unit 34. In the latter case, the control unit 34 can operate one or more devices to control the amount and/or timing of the release of the medication.

As discussed herein, a location of the optoelectronic medical device 64A can be controlled through the skin of an organism body. To this extent, as illustrated in FIG. 10B, an optoelectronic medical device 64B can include on or more mechanisms for placing, moving, and/or maintaining a location of the optoelectronic medical device 64B through the skin of the organism. In particular, the optoelectronic medical device 64B is shown including a set of regions 68A, 68B, which can be affected by an external magnet 70 to locate the optoelectronic medical device 64B as desired. For example, the set of regions 68A, 68B can comprise ferromagnetic material, a magnet, and/or the like. In illustrative embodiments, the optoelectronic medical device 64B can be located in an internal organ 2 of the organism body. Illustrative internal organs include a blood vessel or artery, an intestine, and/or the like.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A device comprising:
a hypodermic needle having an insertion end configured to be inserted subcutaneously into an organism body, wherein the hypodermic needle includes a hollow tube and a plurality of hollow channels embedded in sidewalls of the hollow tube and terminating at the insertion end, the sidewalls with the plurality of channels defining an opening in the hollow tube that extends to the insertion end;
a set of radiation sources configured to generate electromagnetic radiation;
means for directing the electromagnetic radiation generated by the set of radiation sources to a location adjacent to the insertion end of the hypodermic needle, wherein the directing means includes an optical fiber located within one of the plurality of hollow channels embedded in the sidewalls of the hollow tube;
an optoelectronic device configured to sense electromagnetic radiation; and
a wave guiding structure located within another one of the plurality of hollow channels embedded in the sidewalls of the hollow tube, wherein the wave guiding structure is configured to direct electromagnetic radiation from the insertion end of the hypodermic needle to the optoelectronic device.

2. The device of claim 1, wherein the set of radiation sources includes a plurality of light emitting diodes.

3. The device of claim 2, wherein at least one of the plurality of light emitting diodes generates ultraviolet radiation.

4. The device of claim 1, wherein the optoelectronic device comprises at least one sensing device for acquiring fluorescence data corresponding to fluorescence from a surface located adjacent to the insertion end, wherein the at least one sensing device receives the fluorescence data via the wave guiding structure.

5. The device of claim 4, further comprising means for operating the set of radiation sources, wherein the operating means is configured to compare fluorescence spectra and/or intensity of the received fluorescence data to a pre-recorded etalon, and wherein the operating means is configured to adjust at least one of: radiation intensity or a target dose of the electromagnetic radiation generated from the set of radiation sources that is directed to the location adjacent the insertion end based on the comparison of the fluorescence data with the pre-recorded etalon.

6. The device of claim 1, further comprising a syringe fluidly attached to the hypodermic needle, and wherein the syringe is configured to extract fluid from the insertion end and/or deliver fluid to the insertion end via the opening in the hollow tube.

7. The device of claim 6, wherein the delivered fluid comprises a chemical substance activated by the electromagnetic radiation.

8. A system comprising:
a set of radiation sources configured to generate electromagnetic radiation;
means for placing an emission location for the electromagnetic radiation to a target location within an organism body through the skin of the organism body, wherein the means for placing includes:
a hypodermic needle having an insertion end configured to be inserted subcutaneously into an organism body, wherein the hypodermic needle includes a hollow tube and a set of hollow channels embedded in sidewalls of the hollow tube and terminating at the insertion end, the sidewalls with the plurality of channels defining an opening in the hollow tube that extends to the insertion end;
an optical fiber located within at least one of the set of hollow channels embedded in the sidewalls of the hollow tube, wherein the optical fiber is configured to direct the electromagnetic radiation out of the insertion end of the hypodermic needle during the medical procedure;
an optoelectronic device configured to sense electromagnetic radiation;
a wave guiding structure located within another one of the set of hollow channels embedded in the sidewalls of the hollow tube, wherein the wave guiding structure is configured to direct electromagnetic radiation from the insertion end of the hypodermic needle to the optoelectronic device; and
a computer system configured to operate the set of radiation sources to perform a medical procedure on the organism body using the sensed electromagnetic radiation.

9. The system of claim 8, wherein the electromagnetic radiation includes ultraviolet radiation.

10. The system of claim 9, wherein the medical procedure includes at least one of: disinfection of an area of the organism body with the ultraviolet radiation; inducing a photo-catalyst reaction with the ultraviolet radiation; or improving production of vitamin D by the organism body with the ultraviolet radiation.

11. The system of claim 8, wherein the electromagnetic radiation includes infrared radiation, and wherein the medical procedure includes destroying cells of the organism body with the infrared radiation.

12. The system of claim 8, wherein the medical procedure includes activating a chemical in the organism body with the electromagnetic radiation.

13. The system of claim 8, wherein the opening in the hollow tube is configured to deliver a first fluid to a location in the organism body near the insertion end and/or extract a second fluid from the location in the organism body.

14. The system of claim 13, further comprising a syringe fluidly connected to the hypodermic needle, wherein the computer system is further configured to operate the syringe to deliver the first fluid to the location in the organism body and/or extract the second fluid from the location as part of the medical procedure.

15. A device comprising:
a syringe configured to store a fluid;
a set of radiation sources configured to generate electromagnetic radiation;
a needle fluidly connected with the syringe, wherein the needle includes a hollow tube and a plurality of hollow channels embedded in sidewalls of the hollow tube and terminating at an insertion end, the sidewalls with the plurality of channels defining an opening in the hollow tube that extends to the insertion end, wherein the syringe is configured to at least one of: deliver or acquire, fluid through the opening of the hollow tube, and wherein the needle includes an optical fiber located within another one of the plurality of hollow channels embedded in the sidewalls of the hollow tube to deliver electromagnetic radiation to a location adjacent to the insertion end of the needle;
an optoelectronic device configured to sense electromagnetic radiation; and
a wave guiding structure located within an additional one of the plurality of hollow channels embedded in the sidewalls of the hollow tube, wherein the wave guiding structure is configured to direct electromagnetic radiation from the location adjacent to the insertion end of the needle to the optoelectronic device.

16. The device of claim 15, further comprising a computer system configured to operate the set of radiation sources and the syringe to perform a medical procedure on an organism body using the needle.

17. The device of claim 1, further comprising a radiation coupler operatively coupled to the set of radiation sources and the directing means, wherein the radiation coupler guides the electromagnetic radiation from the set of radiation sources to the directing means.

18. The device of claim 17, wherein the radiation coupler comprises a radiation coupler wave guiding structure having a set of sub wave guiding structures each coupled to the radiation sources and a merging sub-wave guiding structure that merges the electromagnetic radiation from each of the sub wave guiding structures to a single beam of electromagnetic radiation that passes through the directing means.

19. The device of claim 1, wherein the wave guiding structure comprises a compound wave guiding structure including physically separate wave guiding structures, each of the physically separate wave guiding structures configured to guide radiation for a specific purpose, wherein at least one of the physically separate wave guiding structures guides radiation for sensing purposes and another one of the physically separate wave guiding structures guides radiation for emitting purposes.

20. The device of claim 5, wherein the operating means is further configured to direct the set of radiation sources to generate pulses of electromagnetic radiation towards the surface adjacent the insertion end via the directing means, receive fluorescence data from the optoelectronic device that is acquired by the at least one sensor from the surface in response to being irradiated by the set of radiation sources, and determine a time between each pulse of electromagnetic radiation and detection of the fluorescence data.

\* \* \* \* \*

UNITED STATES PATENT AND TRADEMARK OFFICE
CERTIFICATE OF CORRECTION

PATENT NO. : 10,688,312 B2
APPLICATION NO. : 15/388296
DATED : June 23, 2020
INVENTOR(S) : Michael Shur and Alexander Dobrinsky Page 1 of 1

It is certified that error appears in the above-identified patent and that said Letters Patent is hereby corrected as shown below:

In the Claims

In Column 12, Line 60, Claim 15, "within another one of the plurality of hollow channels" should be changed to "within one of the plurality of hollow channels".

Signed and Sealed this
Fourth Day of August, 2020

Andrei Iancu
*Director of the United States Patent and Trademark Office*